(12) United States Patent
Lemaire

(10) Patent No.: US 7,285,100 B2
(45) Date of Patent: Oct. 23, 2007

(54) METHOD AND EQUIPMENT FOR ANALYSING BIOLOGICAL SIGNALS REPRESENTING INTERCRANIAL PRESSURE AND BLOOD PRESSURE VARIATIONS

(75) Inventor: Jean-Jacques Lemaire, Saint Genes Champanelle (FR)

(73) Assignee: Universite d'Auvergne-Clermont-Ferrand 1 (FR)

( * ) Notice: Subject to any disclaimer, the term of this patent is extended or adjusted under 35 U.S.C. 154(b) by 22 days.

(21) Appl. No.: 10/484,565

(22) PCT Filed: Jul. 23, 2002

(86) PCT No.: PCT/FR02/02632

§ 371 (c)(1),
(2), (4) Date: Apr. 8, 2004

(87) PCT Pub. No.: WO03/010617

PCT Pub. Date: Feb. 6, 2003

(65) Prior Publication Data

US 2004/0158160 A1    Aug. 12, 2004

(30) Foreign Application Priority Data

Jul. 23, 2001   (FR)   ................................. 01 09807

(51) Int. Cl.
*A61B 5/00* (2006.01)
*A61B 5/02* (2006.01)
(52) U.S. Cl. .................. 600/561; 600/301; 600/485
(58) Field of Classification Search .............. None
See application file for complete search history.

(56) References Cited

U.S. PATENT DOCUMENTS

| 4,893,630 A |   | 1/1990 | Bray, Jr. |
|---|---|---|---|
| 5,482,049 A | * | 1/1996 | Addiss et al. ............... 600/486 |
| 5,666,960 A | * | 9/1997 | Fredberg et al. ............ 600/529 |
| 6,120,442 A | * | 9/2000 | Hickey ....................... 600/300 |

FOREIGN PATENT DOCUMENTS

WO   WO 01/37724 A   5/2001

OTHER PUBLICATIONS

Yves Meyer et al., "L'analyse par ondelettes," Science, Sep. 1987, pp. 28-37.
Keita Hara et al., "Detection of the B waves in the oscillation of intercranial pressure by fast Fourier transform," Med. Inform., 1990, vol. 15, No. 2, pp. 125-131.
J.-J. Lemaire et al., "A computer software for frequential analysis of slow intracranial pressure waves," Computer Methods and Programs in Biomedicine 42, 1994, pp. 1-14.
Metin Akay et al., "Spatial Mapping of Respiratory Related Evoked Responses Using Wavelet Transform Method," Proceedings of the First Joint BMES/EMBS Conference: Serving Humanity, Advancing Technology, Oct. 13-16, 1999, Atlanta, Georgia, USA.

* cited by examiner

*Primary Examiner*—Max F. Hindenburg
*Assistant Examiner*—Patricia Mallari
(74) *Attorney, Agent, or Firm*—DLA Piper US LLP

(57) ABSTRACT

A system for representation and analysis of pressure variables in a patient including a plurality of pressure sensors; a signal processor connected to process signals emitted by the sensors, wherein the process comprises a multiplicity of inputs for receiving analog signals from the sensors, wherein each input is connected to a sampling circuit providing a digital signal used by a calculator for performing processing steps comprising: resampling displayed or recorded signals, analyzing the frequency of sampled signals in relation to a range of target frequencies recorded in a memory, for the display and recording of temporal variations of the signals corresponding to slow waves of the signals, and determination of temporal shifts between the slow waves corresponding to two distinct inputs; and a display that shows variations in the signals.

5 Claims, 2 Drawing Sheets

METHOD AND EQUIPMENT FOR ANALYSING BIOLOGICAL SIGNALS REPRESENTING INTERCRANIAL PRESSURE AND BLOOD PRESSURE VARIATIONS

RELATED APPLICATION

This application is a §371 of International Application No. PCT/FR02/02632, with an international filing date of Jul. 23, 2002 (WO 03/010617, published Feb. 6, 2003), which is based on French Patent Application No. 01/09807, filed Jul. 23, 2001.

FIELD OF THE INVENTION

This invention pertains to the field of methods and equipment for the analysis of biological signals representative of variations in intracranial pressure and blood pressure, and notably for the blood pressure in the cranium.

BACKGROUND

The purpose of such analyses is to assist the clinician in the interpretation of data provided by sensors providing signals representative of the intracranial pressure (ICP) and linked signals, the blood pressure, the arterial or venous circulation rate and the gas concentrations. They enable the clinician to deduce from them the suitable treatments for the pathology deduced from these information elements. These analyses have been the object of various scientific studies, e.g.:

Lemaire et al., "A computer software for frequency analysis of slow intracranial pressure waves", Comput. Methods Programs Biomed., 1984, 42, 1-14.

Daley et al., "Fluctuations of intracranial pressure associated with the cardiac cycle", Journal of Neurosurgery, vol. 11, no. 5, 11-1982, pp. 617-621.

Avezaat et al., "Cerebrospinal fluid pulse pressure and intracranial volume-pressure relationships", J. Neurol., Neurosurg. and Psych., 1979, 42, 00. 687-700.

Portnoy et al., "Cerebrospinal fluid pulse wave as an indicator of cerebral neuroregulation", J. Neurosur., vol 56, 5-1982, pp. 666-678.

Equipment for the acquisition and processing of pressure signals to perform such analyses have been proposed in the state of the art. For example, WO 132076 describes a surveillance device that can determine a physiological parameter in a patient. This device comprises a calibration device configured to provide a calibration signal that is representative of the physiological parameter. A noninvasive sensor is placed on the vessel, with this noninvasive sensor being configured to detect a blood parameter and to produce a signal that is representative of the blood parameter. Thus, there is defined in this context a blood parameter such as pressure, flow rate, volume, velocity, movement and position of the vessel wall and other related parameters. A processor is configured to determine the relationship existing between a characteristic of the excitatory wave received and a characteristic of the physiological parameter.

WO 98/49934 describes a device and a noninvasive method for the measurement of intracranial pressure. The measurement system emits acoustic signals traversing the cranium by means of transmitters and provides an indication of the intracranial pressure as a function of the acoustic signal received after interaction with the brain. Properties such as the impedance of the acoustic transmission, resonance frequency, resonance characteristics, sound velocity and other can be measured and correlated with the intracranial pressure. For example, the acoustic signals have characteristic frequencies of at least 100 kHz, in audible and infrasonic fields. The intensity of the acoustic signal used to measure the intracranial pressure is relatively weak from which derives the possibility of health risks during short or long examinations.

WO 068647 pertains to a method enabling surveillance in a noninvasive manner of the intracranial pressure of a patient. One obtains at least one oscillogram representing a pulsation of an anatomical characteristic of the patient's head, preferable integrating ultrasound reflection traces in a temporal gate corresponding to the reflections of said characteristic. The anatomical characteristic is preferably the third cerebral ventricle. One infers a quantitative measurement of the intracranial pressure from at least two diagnostic characteristics, such as the diagnosis times, associated with the oscillogram. In a variant, one obtains a qualitative measurement of the intracranial pressure from the shape of the respiratory curve imposed on the wave path by the patient's respiration.

WO 99/26529 describes a fast Fourier transform processing unit applied to waveform frequency analysis (MHj) without corporeal movement and provides waveform analysis data (MKD). In parallel, a descendent wave extraction unit and a wave extraction unit linked to an incisure provide, respectively, descendent wave data (tide wave data, TWD) and incisure-linked dicrotic wave data (dicrotic wave data, DWD), which represent, respectively, a descendent wave and a incisure-linked dicrotic wave. A pulse evaluation unit then provides data relative to the pulse status (ZD) on the basis of TWD and DWD data, by means of which a notification unit establishes a report on the status of the pulse of the subject under consideration.

Also known is U.S. Pat. No. 4,893,630 describing equipment and a method for the analysis of the pressure in a living organ by a sensor delivering an analog signal, comprising an analog-digital converter and an analysis by Fourier transform to emit a distribution of the signal frequencies provided by the pressure sensors.

These different solutions are not completely suitable for the provision of particular information useful for the clinician.

SUMMARY OF THE INVENTION

This invention relates to a system for representation and analysis of pressure variables in a patient including a plurality of pressure sensors; a signal processor connected to process signals emitted by the sensors, wherein the processor includes a multiplicity of inputs for receiving analog signals from the sensors, wherein each input is connected to a sampling circuit providing a digital signal used by a calculator for performing processing steps including resampling displayed or recorded signals, analyzing the frequency of sampled signals in relation to a range of target frequencies recorded in a memory, for the display and recording of temporal variations of the signals corresponding to slow waves of the signals, and determination of temporal shifts between the slow waves corresponding to two distinct inputs; and a display that shows variations in the signals.

BRIEF DESCRIPTION OF THE DRAWINGS

Better understanding of the invention will be obtained from the description below with reference to a nonlimitative example of implementation in which.

DETAILED DESCRIPTION

Figure 1:
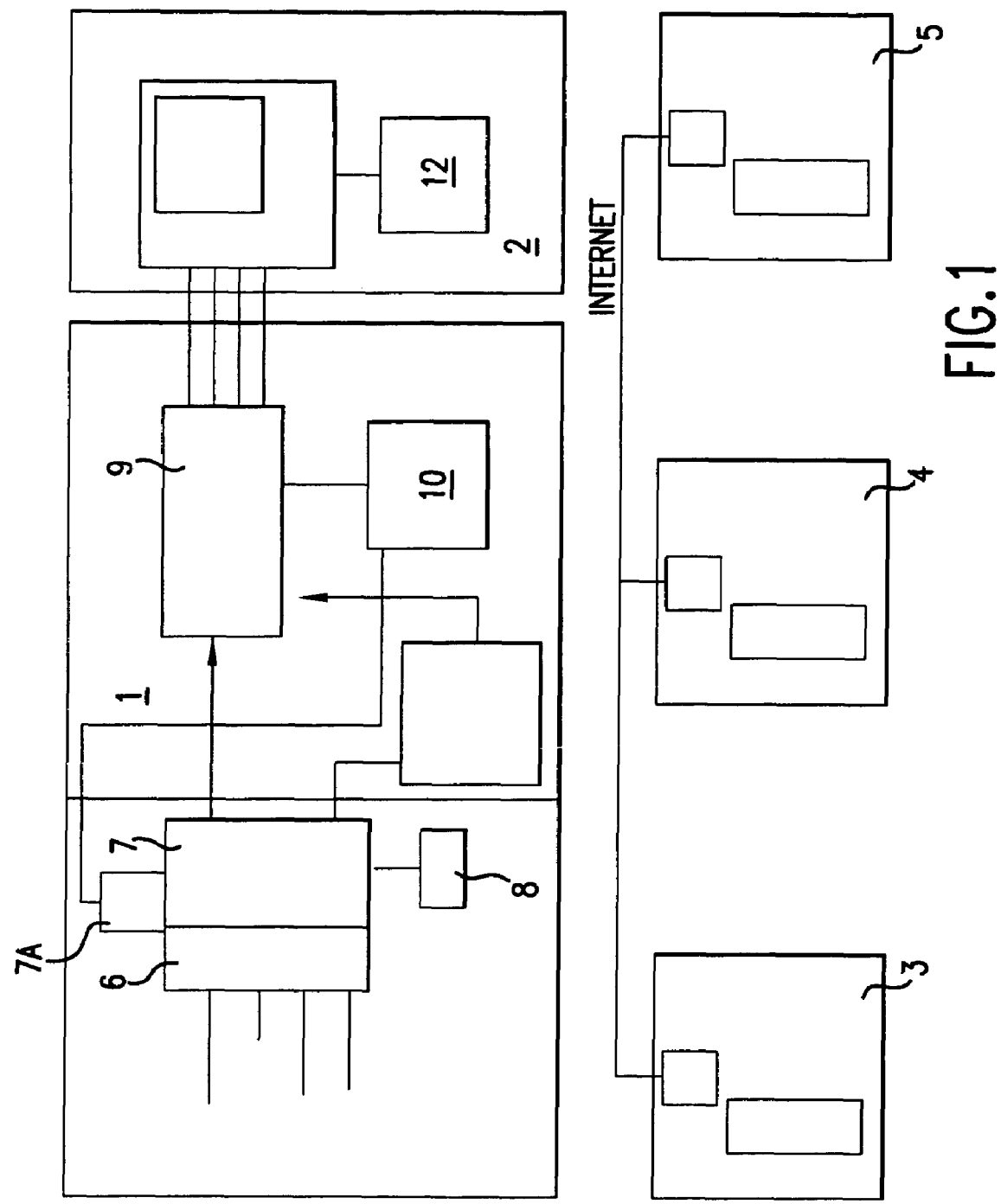
FIG. 1 is a schematic view of a system according to the invention.

This invention resolves the problems described above by providing a system for the representation and analysis of pressure variables comprising pressure sensors, means for processing the signals emitted by the sensors and means for displaying variations in the signals, characterized in that the processing means comprise a multiplicity of inputs for receiving analog signals stemming from the different sensors, each input being connected to a sampling circuit providing a digital signal used by a calculator for performing processing steps comprising:

resampling the signals for the expansion of the displayed or recorded signal, frequency analysis of the sampled signal in relation to a range of target frequencies recording in a memory, for the display and recording of the temporal variations of the signals corresponding to the slow waves, and determination of the temporal shift between the signals corresponding to two distinct inputs.

The frequency analysis for the extraction of the information relative to the slow waves constitutes an essential improvement of the equipment of the prior art because it offers the clinician new interpretation possibilities.

According to a first variation, the frequency analysis means are constituted of a calculator applying Fast Fourier Transform (FFT). According to a second variant, the frequency analysis means are constituted of a calculator applying wavelet analysis. The range of recorded target frequencies advantageously comprises frequencies comprised between $8 \times 10^{-3}$ hertz and $50 \times 10^{-3}$ hertz.

According to a preferred mode of implementation, the system comprises a sampling circuit performing a sampling of each of the input signals at a first frequency and a resampling circuit at a sampling frequency lower than the first frequency for recording the time-stamped signals in a memory. According to another variant, the invention comprises a module for the acquisition and processing of the local signals and at least one remote monitoring station connecting to the local acquisition module by a telecommunication network.

The invention also pertains to a method for the analysis of biological pressure signals comprising a sampling step, characterized in that it also comprises a step of frequency analysis in relation to a range of target frequencies corresponding to type B and UB slow waves.

According to a variant, the methods moreover, comprises a step for the determination of the temporal shift between the signals corresponding to the two distinct inputs.

Turning now to the Drawings, the equipment according to the invention is composed of three principal modules:

- an acquisition module (1), generally located close to the patient,
- a processing module (2) generally located with the clinician,
- an exploitation and display module which can be located close to the patient in the form of an equipment unit (3) or in the form of a local work station (4) connected to the processing network by an internal network or constituted of a remote work station (5) connected to the processing module (2) by a telecommunication network, e.g., the internet.

The first module (1) has a multiplicity of input channels for receiving the signals originating from various pressure sensors: arterial blood pressure (ABP) sensor, cerebral blood flow (CBF) sensor, and intracranial blood pressure (ICP) sensor.

In the example described, module (1) has 8 channels. It comprises an 8-path input-output interface (6) emitting a reference signal and analog signals corresponding to the various channels in parallel or multiplexed form.

The analog signals are then sampled by a circuit (7) controlled by a clock (8). Each signal is preferably sampled at 100 samples by second. It can be displayed directly on the screen of a monitor (9) or be the object of an extraction of one sample out of 8 by a resampling circuit (7A) for recording in a memory (10) in the form of time-stamped digital sequences, forming tables associated with general information (patient's name, practitioner's name, etc.) The module optionally also comprises means for capturing free information in maker form. This information is associated with the recorded information for describing, e.g., an event, or for annotating the curve of an observed signal.

The analysis module (2) performs a frequency analysis of the sampled signals from a target frequency selected from among: type "B" slow waves corresponding to a frequency comprised between $8 \times 10^{-3}$ and $50 \times 10^{-3}$ hertz, infra-B waves corresponding to a frequency lower than $8 \times 10^{-3}$ hertz, and ultra-B waves corresponding to a frequency comprised between $50 \times 10^{-3}$ hertz and $200 \times 10^{-3}$ hertz.

This analysis is performed on blocks of N sampled points (power of two), for example, by blocks of 256 points. The result is recorded in a memory (12). A sampled sequence of a signal comprising M samples is thus translated into a file of M/N points corresponding to the variation of the frequency analysis transform.

The frequency analysis can be performed by Fast Fourier Transform (FFT). It consists of performing a spatial frequency analysis by means of a transform enabling translation of a waveform into the frequency domain. The result of the transform is a succession of coefficients describing the amplitude of each frequency component present in the analyzed block.

The analysis by FFT or by Discrete Cosine Transform (DCT) characterizes each frequency by multiplying the input signal by an example of the target frequency of base function, selected from among the frequencies of the slow waves, and integrating the product obtained.

The analysis is performed with known electronic circuits (DSP) or by application of known algorithms, with a sampling rate determined by the clinician, by selection of one of the observed slow-wave frequencies. The parameter N of the sample number in the analyzed recording is determined in advance, for example 256, or variable by the choice of the user. The discrete Fourier transform algorithms convert a time function of the sampled complex values into a function of complex frequency values, also sampled. They provide information such as: the table of the coefficients of the cosines in the Fourier formula (real part of the result), the table of the coefficients of the sines in the Fourier formula (imaginary part of the result), and the first output element of each of the tables contains the mean value of all of the inputs. The variant of this element is displayed on the monitor and is the object of comparative processing of one signal to another.

Extraction of the slow waves is performed from the amplitude (and power) spectrum and is performed by detection of the frequency (F) the amplitude (or power) of which is maximal (P) and this for the bands of B, UB and JIB frequencies. In the particular, the analysis module (2) comprises means for calculating the shift between the slow waves of two signals and representation on the display monitor of these shifts. This analysis is by application of a coherence function in the frequency domain or by application of a Pearson coefficient in the temporal domain.

Figure 2:
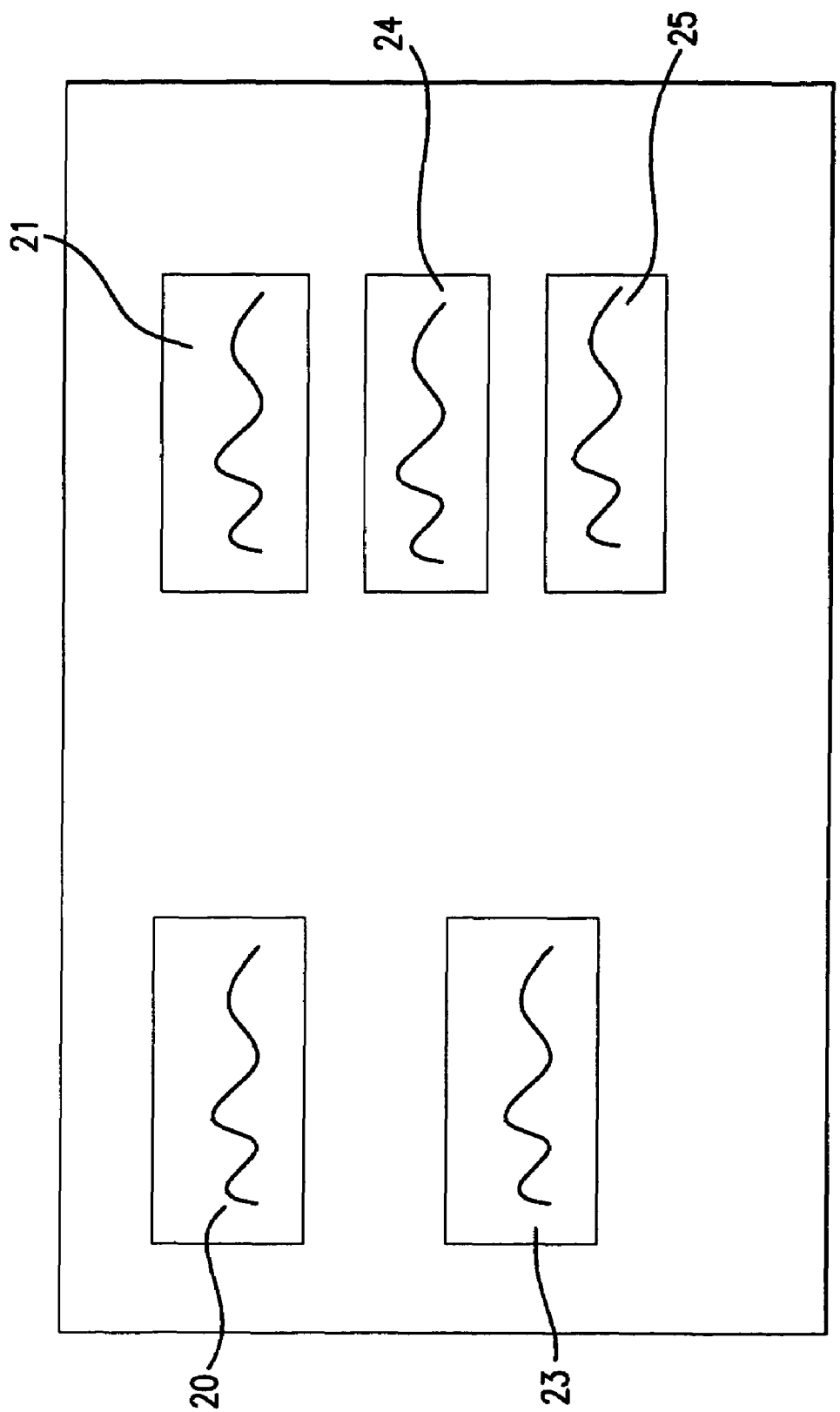
FIG. 2 is a view of a screen for the display of information displayed by the system.

As an example, FIG. 2 is a view of a display screen from a system according to the invention. The screen is subdivided into a multiplicity of display zones for the representation: the temporal variation of the intracranial pressure (zone (20)), the temporal variation of the arterial pressure (zone (21)), the variation of the component corresponding to the slow wave B with a curve (22) corresponding to the frequency in millihertz and a curve (23) corresponding to the amplitude of the pressure, correlation rate between the intracranial pressure signals (or the circulatory rate (20) and arterial pressure (21)) in the form of the curve (24), and temporal shift between the slow waves of the intracranial pressure or circulatory rate (20) and arterial pressure (21), in the form of the curve (25).

The invention claimed is:

1. A system for representation and analysis of pressure variables in a patient comprising:
   a plurality of pressure sensors generating analog signals;
   a signal processor comprising a multiplicity of inputs for receiving said analog signals from the sensors, said signal processor comprising a sampling circuit for sampling said analog signals at a first frequency and for providing sampled digital signals at said first frequency;
   a resampling circuit at a sampling frequency lower than the first frequency for recording time-stamped signals in a memory;
   a calculator that processes said sampled digital signals, said processing comprising:
      analyzing the frequency of said sampled digital signals in relation to a range of target frequencies recorded in a memory, said target frequencies comprising at least slow waves frequencies;
      recording temporal variations of said sampled digital signals corresponding to slow waves of said sampled digital signals, and
      determining temporal shifts between slow waves corresponding to two distinct inputs of the multiplicity of inputs; and
   a display for displaying variations of said sampled digital signals and for displaying said temporal shifts between slow waves corresponding to the two distinct inputs.

2. The system according to claim 1, further comprising a module for acquisition and processing of local signals and at least one remote monitoring station connected to said local acquisition module by a communication network.

3. The system according to claim 1, wherein said calculator performs frequency analysis by applying a Fast Fourier Transform (FFT).

4. The system according to claim 1, wherein the calculator performs frequency analysis by applying a wavelet analysis.

5. The system according to claim 1, wherein the range of recorded target frequencies comprises frequencies between $8\times10^{-3}$ hertz and $50\times10^{-3}$ hertz.

* * * * *